US009101725B2

(12) United States Patent
Plouvier et al.

(10) Patent No.: US 9,101,725 B2
(45) Date of Patent: Aug. 11, 2015

(54) PREFILLABLE DRUG DELIVERY DEVICE

(71) Applicant: BECTON DICKINSON FRANCE, Le Pont de Claix (FR)

(72) Inventors: Adrien Plouvier, Saint Martin d'Heres (FR); Frederic Perot, Saint Paul de Varces (FR); Romain Lanier, Veury-Voroize (FR)

(73) Assignee: Becton Dickinson France, Le Pont-de-Claix (FR)

( * ) Notice: Subject to any disclaimer, the term of this patent is extended or adjusted under 35 U.S.C. 154(b) by 0 days.

(21) Appl. No.: 13/926,443

(22) Filed: Jun. 25, 2013

(65) Prior Publication Data

US 2013/0345631 A1    Dec. 26, 2013

(30) Foreign Application Priority Data

Jun. 25, 2012   (EP) ..................... 12305732

(51) Int. Cl.
*A61M 5/32*     (2006.01)
*A61M 5/00*     (2006.01)
*A61M 5/28*     (2006.01)
*A61M 5/31*     (2006.01)
*A61M 5/315*    (2006.01)

(52) U.S. Cl.
CPC ............... *A61M 5/326* (2013.01); *A61M 5/001* (2013.01); *A61M 5/283* (2013.01); *A61M 5/3221* (2013.01);
(Continued)

(58) Field of Classification Search
CPC ......... A61M 5/00; A61M 5/178; A61M 5/24; A61M 5/2429; A61M 5/28; A61M 5/283; A61M 5/3135; A61M 5/3137; A61M 5/3146; A61M 5/315; A61M 5/3202; A61M 5/3205; A61M 5/321; A61M 5/3213; A61M 5/3219; A61M 5/322; A61M 5/3221; A61M 5/3232; A61M 5/3234; A61M 5/3243; A61M 5/3245; A61M 5/326; A61M 5/001; A61M 5/3148; A61M 2005/31506; A61M 2005/31508; A61M 2005/3247; A61M 2005/3261; A61M 2005/3263; A61J 1/20
USPC ............ 604/110, 162, 164.08, 181, 187, 192, 604/193, 194, 195, 196, 197, 198, 199, 200, 604/201, 202, 203, 206, 218, 219, 231, 232, 604/263
See application file for complete search history.

(56) References Cited

U.S. PATENT DOCUMENTS 2,574,339 A   11/1951   Lockhart
3,841,329 A   10/1974   Killinger
(Continued)

FOREIGN PATENT DOCUMENTS

EP    0111796 B1    5/1986
EP    0146558 B1    8/1988
(Continued)

OTHER PUBLICATIONS

Denning, G., "Turning Prefilled Upside Down", 2012, pp. 4-6, Frederick Furness Publishing.

*Primary Examiner* — Bhisma Mehta
*Assistant Examiner* — Nicholas Meghri
(74) *Attorney, Agent, or Firm* — The Webb Law Firm (57) ABSTRACT

The present invention relates to a prefillable drug delivery device having a housing receiving a needle hub which is movable with respect to said needle hub between a retracted position and a protection position. The device also includes a tubular barrel intended to receive a drug that is pre-mountable on said housing so that said needle hub closes its distal end. The device further includes a sealing member actionable once said tubular barrel is pre-assembled on said housing, capable of transitioning from an inactive state where no sealing contact is present between said needle hub and said tubular barrel, to an active state, in which sealing contact is performed. In the active state of said sealing member, said tubular barrel is movable in translation with respect to said needle hub between a proximal position and a distal position, for realizing delivery of the drug.

20 Claims, 6 Drawing Sheets

(52) U.S. Cl.
CPC ........... *A61M 5/3243* (2013.01); *A61M 5/3148* (2013.01); *A61M 5/3245* (2013.01); *A61M 2005/31506* (2013.01); *A61M 2005/31508* (2013.01); *A61M 2005/3247* (2013.01); *A61M 2005/3261* (2013.01); *A61M 2005/3263* (2013.01)

(56) References Cited

U.S. PATENT DOCUMENTS

| | | |
|---|---|---|
| 3,980,083 A | 9/1976 | Elliott |
| 4,741,737 A | 5/1988 | Meyer et al. |
| 4,809,711 A | 3/1989 | Meyer et al. |
| 5,478,324 A * | 12/1995 | Meyer ............ 604/203 |
| 6,007,520 A * | 12/1999 | Sudo ............ 604/181 |
| 2004/0116853 A1 | 6/2004 | Halseth et al. |
| 2006/0178644 A1* | 8/2006 | Reynolds ............ 604/232 |
| 2010/0198165 A1* | 8/2010 | Zihlmann et al. ............ 604/208 |

FOREIGN PATENT DOCUMENTS

| | | | |
|---|---|---|---|
| EP | 684846 B1 | 5/1999 | |
| EP | 1079877 B1 | 12/2005 | |
| FR | EP 1079877 B1 * | 12/2005 | ............ A61M 5/24 |
| WO | 9218178 A1 | 10/1992 | |

* cited by examiner

PREFILLABLE DRUG DELIVERY DEVICE

The present invention relates to a prefillable drug delivery device capable of receiving an integrated safety system.

In this application, the distal end of a component or of a device means the end furthest away from the hand of the user and the proximal end means the end closest to the hand of the user, when the component or device is in the in-use position. Similarly, in this application, the terms "in the distal direction" and "distally" mean in the direction of the injection or of the delivery of the product, and the terms "in the proximal direction" and "proximally" mean in the direction opposite to the direction of injection.

Pre-filling injectable drugs has become a mainstream standard over the course of the last few years. Initially used mainly for vaccines, this concept can now be found in many other therapeutic classes. Prefilled drug delivery devices have a lot of advantages: they are convenient and easy to use. The dosage form is safe. It is easy to identify the drug contained therein. The dead space is very low: as such, potential waste of usually expensive product is limited.

These prefilled drug delivery devices should preferably be provided with needle safety systems in order to avoid accidental needlestick injuries before delivery and after delivery of the drug, in particular with respect to healthcare workers.

Prefilled drug delivery devices need to be prefilled by the pharmaceutical companies producing the drug, in particular within the companies' own premises. Pharmaceutical companies try to provide prefilled drug delivery devices with needle safety system. Nevertheless, adding safety features to a drug container should not impact the drug delivery functions.

Usually, the container and the needle safety system are provided separately to the pharmaceutical companies. The pharmaceutical company fills the container with the adequate drug, closes the container with a stopper, and then assembles the needle safety system on the prefilled container. However, the pharmaceutical company must store two sets of products, the containers on one hand and the needle safety systems on the other hand. Moreover, this requires an additional operation for the pharmaceutical company, which must proceed to the assembly of the needle safety system on the prefilled container on its site, with risks that the needle safety system be incorrectly assembled. This is a waste of time for the pharmaceutical companies.

Safety systems from the prior art may also increase the global size of the drug delivery system, which yields to higher cost of transport and storage, and requires modifications by the pharmaceutical companies of their pre-filling system.

There is therefore a need for a drug delivery device which would be prefillable and which at the same time would already comprise its own needle safety system, without an important increase of the global size of the drug delivery device with respect to the drug delivery device without the safety system. The pharmaceutical companies provided with such a device would simply have to fill it with the adequate drug, and the drug delivery device would then be readily available for end-users in hospitals or officines, without the need for the pharmaceutical companies to assemble an additional needle safety system on the prefilled container and without further storage and transportation costs.

There is therefore a need for a prefillable drug delivery device capable of having a small sized integrated needle safety system.

The present invention aims at providing such a prefillable drug delivery device.

A first aspect of the invention is a prefillable drug delivery device, comprising:
  a housing at least partially receiving a needle hub, said housing being movable with respect to said needle hub between a retracted position, in which a distal end of said needle hub extends beyond the distal end of said housing, and a protection position, in which the distal end of said needle hub does not extend beyond the distal end of said housing,
  a tubular barrel for receiving a drug, said tubular barrel being capable of being pre-assembled on said housing via its distal end so that at least part of said needle hub substantially closes the distal end of said tubular barrel, said tubular barrel being movable in translation and/or in rotation along said longitudinal axis with respect to said needle hub and to said housing,
wherein said device further comprises sealing means actionable once said tubular barrel is pre-assembled on said housing, said sealing means being capable of going from an inactive state in which no sealing contact is present between said part of said needle hub and an inner wall of said tubular barrel, to an active state, in which sealing contact is performed between said part of said needle hub and the inner wall of said tubular barrel,
  wherein, in the active state of said sealing means, said tubular barrel is movable in translation with respect to said needle hub between a filling position, in which the tubular barrel may be filled with the drug to be delivered, and an end-of-delivery position, distally spaced with respect to said filling position, in which said drug potentially received within said tubular barrel has been substantially expelled from said tubular barrel via said needle.

The tubular barrel of the device of the invention is preferably open at both its distal and proximal end, i.e. it has mainly the shape of a tube. In other words, no transversal wall is present at the proximal end and at the distal end of the tubular barrel. In the device of the invention, the needle hub realizes the distal closure of the tubular barrel intended to receive the drug. As long as the sealing means are in their inactive state, this distal closure is not tight and may allow the passage of a liquid or gas. Indeed, such passage may be required in order to allow the sterilization of the device when ethylene oxide or heated vapor are used for the gas sterilization. Once the sealing means have been activated, the needle hub acts as a tight distal closure of the tubular barrel, so that no liquid product may be allowed to pass between the needle hub and the inner wall of the tubular barrel. As will appear from the description below, the needle hub is nevertheless provided with a channel for receiving the needle providing a passageway for the drug contained in the tubular barrel to be expelled out of the tubular barrel, so that delivery of the drug may be completed.

Although the prefillable drug delivery device of the invention may be stored under the form of a kit of parts, with the tubular barrel on one hand and the rest of the device on the other hand, it is preferably provided to the pharmaceutical company with the tubular barrel already pre-assembled on the housing, the sealing means being in their inactive state. The pharmaceutical company may then activate the sealing means so as to put the tubular barrel in a sealed state with respect to the needle hub in order to proceed to the filling of the tubular barrel with the adequate drug.

As will appear in the description below, because of its structure and arrangement, the prefillable drug delivery device of the invention is capable of receiving a needle safety system that will not interact with the filling operations performed on the site of the pharmaceutical company. Indeed, the prefillable drug delivery device may comprise a needle safety system, regardless from the fact that it is already filled or not. Indeed, in the device of the invention, the needle safety system is under the form of a housing which is provided on the drug delivery device from the start, and which does not interact with the tubular barrel during the filling step of the tubular barrel. Therefore, the tubular barrel of the drug delivery device of the invention may be filled with the adequate drug, while the needle safety system is already assembled on the drug delivery device: the filling step has no consequence on the integrity of the housing. In other words, the presence of the integrated needle safety system, i.e. the housing, does not perturb the filling step. The drug delivery device of the invention is provided to the pharmaceutical companies with the needle safety system already provided on the device: the pharmaceutical companies therefore do not have to deal with the step of assembling the needle safety system on the device. This means improved easiness of the filling step for these companies and gains in productivity. Moreover, the prefillable drug delivery device according to the invention has a global size similar to standard prefillable drug delivery devices without safety systems.

The drug delivery device of invention may also consist in a reduced number of parts and may be assembled with a few steps process. This allows a high productivity and a low cost for the drug delivery system.

In the drug delivery device of the invention, the integrity of the drug may be easily checked by the pharmaceutical companies or by the health-care worker performing the injection. Indeed, as the pharmaceutical drug is contained in a tubular barrel, without any system or shield positioned around, the control of the content of the delivery device is easy and efficient.

In embodiments, said housing having a longitudinal axis, said needle hub bears a needle, said needle hub and needle being substantially aligned on said longitudinal axis, a distal end of said needle extending beyond the distal end of said housing when said housing is in its retracted position, the distal end of said needle not extending beyond the distal end of said housing when said housing is in its protection position.

In embodiments, the device further comprises temporary holding means for maintaining said tubular barrel pre-assembled on said housing before activation of the sealing means. "Temporary holding means" means herein that the temporary holding means are sufficient for preventing the tubular barrel to separate from the housing under the effect of simple gravitation and/or the common movements that may be generated by the handling, the manipulation and transportation of the prefillable drug delivery device when the tubular barrel is in the pre-assembled position on the housing. Nevertheless, said temporary holding means do not prevent the rotation and/or translation of the tubular barrel with respect to the needle hub when a sufficient deliberate force is exerted on said tubular barrel with respect to the housing and/or the needle hub.

In embodiments, the sealing means are designed so that they are caused to go from their inactive state to their active state under the effect of a limited movement of said tubular barrel with respect to said needle hub. "Limited movement" means herein that the tubular barrel may be rotated and/or translated with respect to the needle hub on a small distance: for example, the tubular barrel may be rotated of less than 360° with respect to the needle hub and/or translated on a distance ranging from a few millimeters to 1 or 2 centimeters with respect to the needle hub along the longitudinal axis, in particular in the distal direction, in order to put the sealing means in their active state.

In embodiments, said temporary holding means comprises an outer rim located on the outer wall of the distal part of the tubular barrel and an annular recess located on an inner wall of said housing, said outer rim being engaged in said annular recess when said tubular barrel is pre-assembled on said housing, said outer rim being disengageable from said annular recess under the effect of said limited movement. For example, said limited movement is a distal movement.

In embodiments, part of the sealing means is located on the tubular barrel and other part of the sealing means is located on the needle hub.

In embodiments, the device further comprises securing means for preventing said sealing means from returning to their inactive state once they are in their active state. Such embodiments confer an improved safety to the device once it has been filled with the drug to be delivered. Thanks to the securing means, the drug, in particular a liquid drug, may not leak out of the tubular barrel via the distal end of said tubular barrel. In embodiments, part of said securing means is located on the tubular barrel and other part of said securing means is located on the housing.

In embodiments, the sealing means comprise a radially compressible part of said needle hub, and a restricted portion of the inner wall of said tubular barrel, said sealing means reaching their active state when said restricted portion is caused to face said radially compressible part under the effect of a limited distal movement of said tubular barrel with respect to the needle hub, said restricted portion thereby compressing said radially compressible part and generating sealing contact between said needle hub and the inner wall of said tubular barrel. In such an active state of the sealing means, as explained above, the needle hub realizes a tight distal closure of the tubular barrel: as such, no liquid product may leak between the radially compressible part of the needle hub and the inner wall of the tubular barrel. However, the radially compressible part of the needle hub, and thus the needle hub, may still be able to slide in translation with respect to the tubular wall, while at the same time realizing said sealing contact. For example, the radially compressible part may be a rubber part or an elastomeric part, such as a stopper.

In embodiments, the securing means comprises said outer rim and a radial ridge distally spaced with respect to said annular recess on the inner wall of said housing, said radial ridge being provided with a sloped proximal face, said outer rim being capable of overcoming said sloped proximal face under the effect of said limited distal movement of said tubular barrel with respect to the needle hub, said outer rim coming thereafter in proximal abutment against said radial ridge once said sealing means are in their active state and a proximal force is exerted on said tubular barrel. The tubular barrel is therefore prevented from being translated back in the proximal direction, and the rubber part of the needle hub may no more escape the restricted portion of the barrel: sealing contact of the tubular barrel with respect to the needle hub is therefore ensured and the user may safely fill the tubular barrel with the drug to be delivered.

In embodiments, the drug delivery device further comprises retaining means for maintaining said housing in its retracted position at least up to the time the tubular barrel reaches its end-of-delivery position. For example, said retaining means may be releasable when the tubular barrel reaches its end-of-delivery position. For example, the retaining means may be the combination of a peg and a recess, the peg being provided on said housing and the recess being provided on said needle hub, or vice-versa, the peg being engaged in the recess for maintaining said housing in its retracted position:

for example, the peg may be released manually by a user at the end of the delivery step, so that the housing may be drawn and extended on the needle in order to avoid accidental needle-stick injuries.

In embodiments, the prefillable drug delivery device further comprises deactivating means for releasing said retaining means when said tubular barrel reaches its end-of-delivery position. For example, in an alternative to the manually release of the peg as described above, the peg may be released from the recess by being deflected by the distal end of the tubular barrel at the end of the delivery step. The user may then manually draw the housing to recover the distal end of the needle.

In embodiments, the drug delivery device further comprises biasing means for automatically moving the housing from its retracted position to its protection position, said biasing means being maintained in a stressed state, in which the housing is in its retracted position, by said retaining means, and being caused to expand to an expanded state, in which said housing is in its protection position, when said retaining means are released. For example, such a biasing means may be a spring that is released at the same time the retaining means are released. Such a spring allows for an automatic movement of the housing, which needs not be completed manually by the user leading to a passive activation of the safety system. In such embodiments, since the safety system is activated automatically at the end of the injection, meaning it is a passive safety system, no further action is needed from the user. No specific training is therefore required to use a drug delivery device according to the present invention.

In embodiments, the retaining means comprises flexible legs located on said housing and capable of being radially deflected from a rest position, in which they maintain said biasing means in their stressed state, to a deflected position, in which the biasing means is free to expand, the deactivating means comprise the distal end of said tubular barrel, said distal end coming in contact with, and radially deflecting, said flexible legs when said tubular barrel reaches its distal position, thereby freeing the biasing means which moves the housing to its protection position. For example, the biasing means is a helical spring coupling together the needle hub and the housing.

In embodiments, the drug delivery device further comprises locking means for preventing said housing from being moved back to its retracted position once it has reached its protection position. Such embodiments provide for an improved safety of the device, as the needle may not be uncovered once the delivery step is completed. Accidental needlestick injuries are therefore avoided.

In embodiments, a proximal end of said needle extends proximally beyond a proximal end of said needle hub. The proximal end of the needle may extend proximally beyond a proximal end of said needle hub at the time the device of the invention is manufactured, or alternatively, it may be caused to extend proximally beyond a proximal end of said needle hub at the time of use of delivery device in order to proceed to the delivery of the drug.

In embodiments, the proximal end of said tubular barrel is further provided with an outer flange intended to form a pushing surface for a user to exert a distal pressure on said tubular barrel, in particular during the delivery step.

Another aspect of the invention is therefore a prefilled drug delivery device comprising a prefillable drug delivery device as described above in which said tubular barrel is assembled on said housing and said sealing means are in their active state, wherein the part of the tubular barrel located proximally to the needle hub is filled with a drug to be delivered, the proximal end of said tubular barrel being closed with a stopper. The tubular barrel therefore forms a safe container for the drug to be delivered, as its distal closure is tightly closed by the needle hub, the sealing means being in their active state, its proximal end being also tightly closed by a stopper.

Embodiments of the present invention will now be described in greater detail based on the following description and the appended drawings in which.

Figure 1:
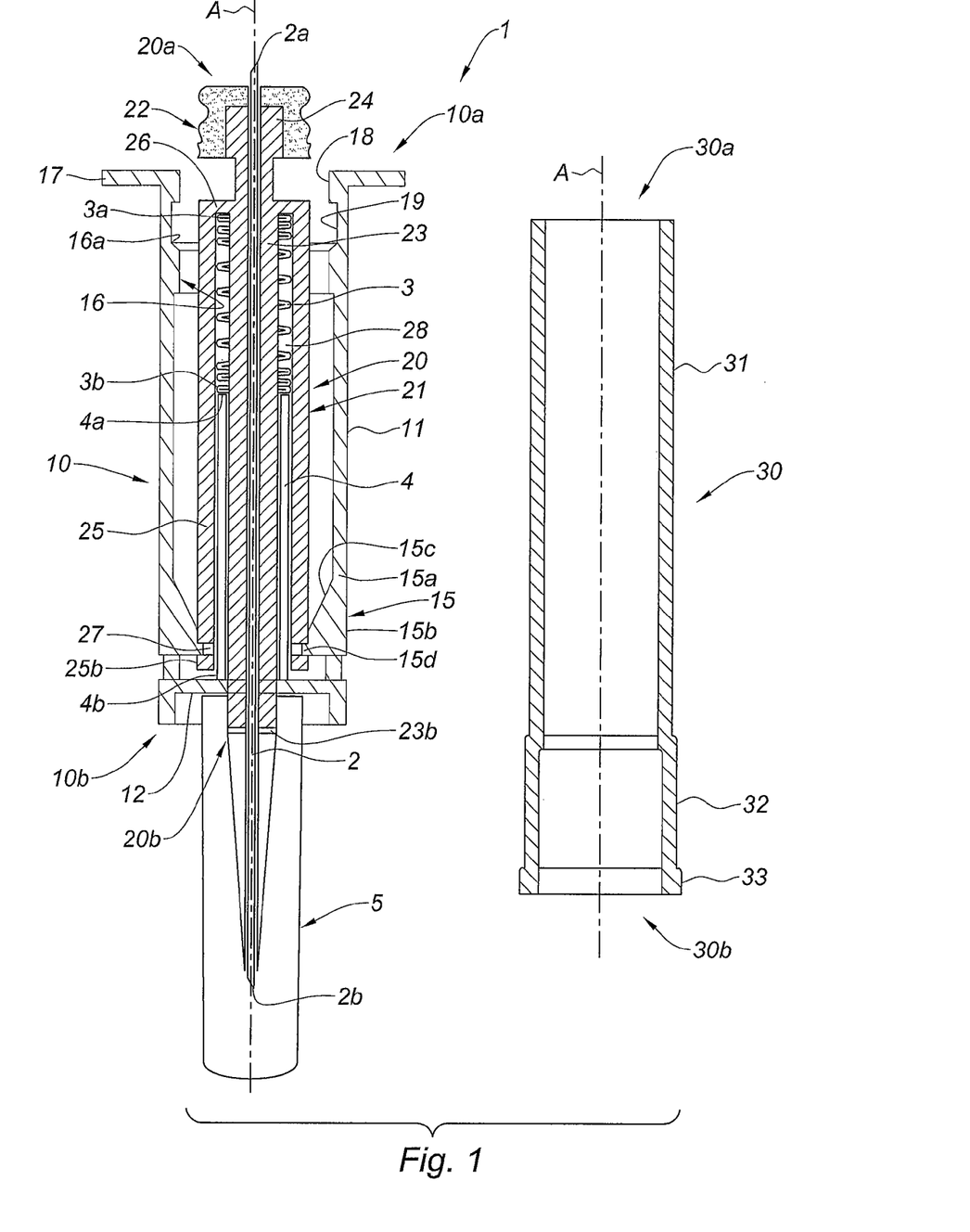
FIG. 1 is a side view of a prefillable drug delivery device of the invention.

With reference to FIG. 1 is shown an embodiment of a prefillable drug delivery device 1 of the invention, under the form of a kit of parts, i.e. comprising a housing 10 and a tubular barrel 30, before the tubular barrel 30 is pre-assembled on the rest of the device 1. The drug delivery device 1 has a longitudinal axis A and comprises on one hand a housing 10 at least partially receiving a needle hub 20 bearing a needle 2 and on the other hand a tubular barrel 30 which may be assembled on the housing 10 in two steps as will appear in the description below. In a first step, the tubular barrel is pre-assembled on the housing with no sealing contact present between the tubular barrel and the needle hub, with sealing means being in an inactive state. In a second step, the sealing means are activated, and the tubular barrel is assembled on the housing, with sealing contact existing between the tubular barrel and the needle hub. On the example shown, the needle 2 has a sharp proximal end 2a and a sharp distal end 2b. On FIG. 1, the device 1 further comprises a biasing means under the form of a helical spring 3, and a sleeve 4, the positions and functions of which will be described in detail later below. On this Figure also, the needle 2 is covered with a protective cap 5.

Figure 2:
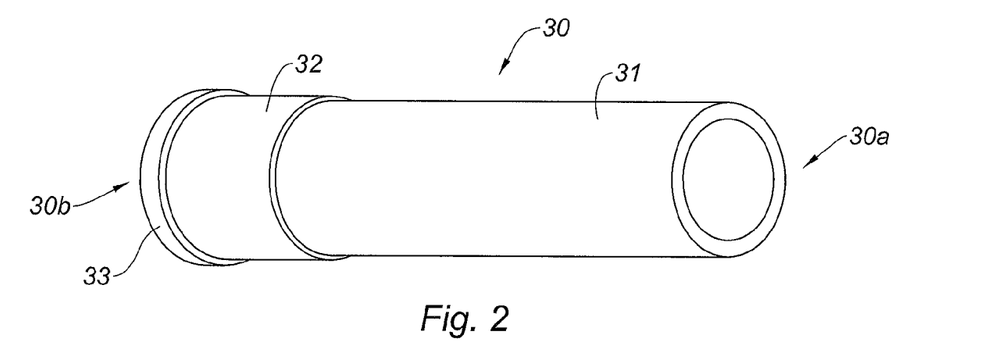
FIG. 2 is a perspective view of the tubular barrel of the device of FIG. 1.

With reference to FIGS. 1 and 2, the tubular barrel will now be described in detail. The tubular barrel 30 has the global shape of a tube fully open at its proximal end 30a and at its distal end 30b. As appears from these Figures, the tubular barrel 30 comprises two portions having different inner diameters. In particular, the tubular barrel 30 comprises a restricted portion 31 having an inner diameter smaller than that of a portion forming the distal region 32 of the tubular barrel 30. The restricted portion 31 therefore extends proximally from the distal region 32 of the tubular barrel 30 and is longer than the distal region 32. As will appear later therein, a substantial part of the restricted portion 31 is intended to form a container for receiving the drug to be filled in the device 1. The tubular barrel 30 further comprises at its distal end 30b a circular outer rim 33 located on its outer wall. The tubular barrel 30 may be made of any material capable of storing a drug, such as glass or plastic. It is preferably transparent so that the user may see the drug contained therein once the device 1 is prefilled.

Figure 3A:
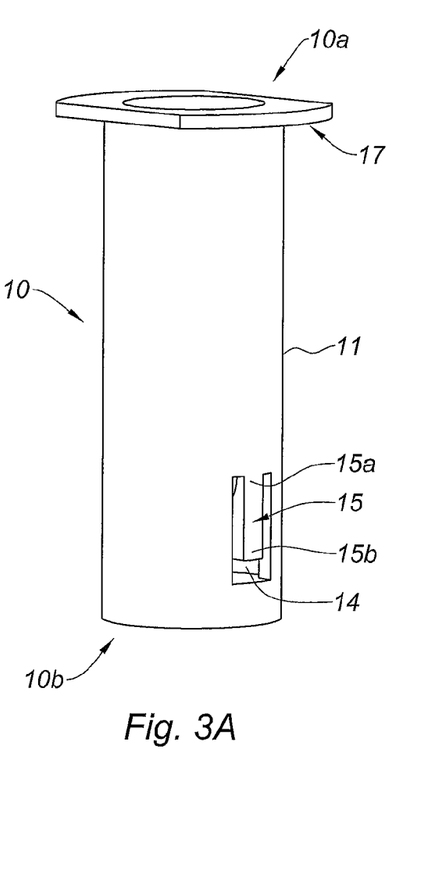
FIG. 3A is a perspective view of the housing of the device of FIG. 1.
Figure 3B:
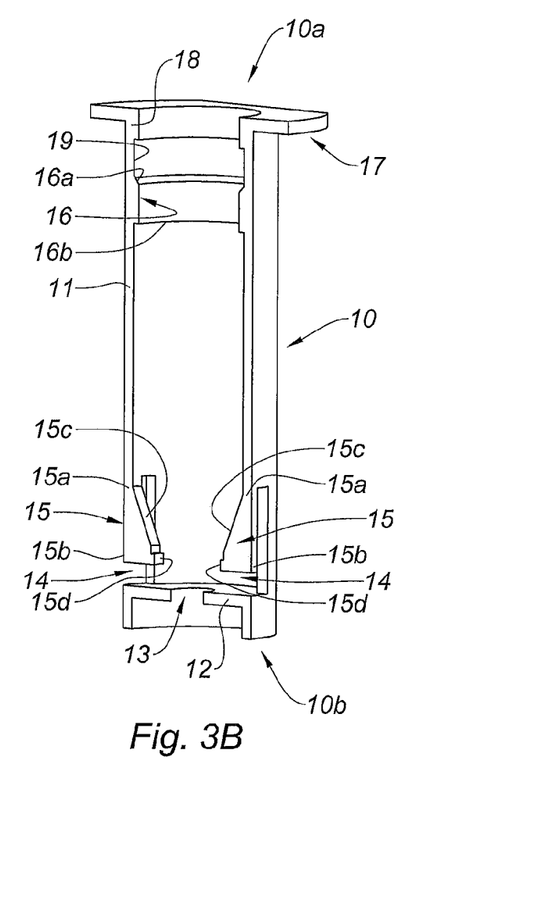
FIG. 3B is a section view of the perspective view of FIG. 3A.

With reference to FIGS. 1, 3A and 3B, the housing 10 will now be described in detail. The housing 10 comprises a globally tubular wall 11 provided in its distal region with an inner transversal wall 12 having a central hole 13. The tubular wall 11 is further provided with two diametrically opposed longitudinal windows 14 which are proximally spaced with respect to the inner transversal wall 12, each window 14 receiving a flexible leg 15 fixed to the tubular wall 11 by its proximal end 15a. The distal end 15b of each flexible leg 15 is free and is capable of being outwardly radially deflected under the effect of an outer radially force exerted thereon. In addition, each flexible leg 15 is provided with a sloped proximal face 15c and with an inner radial peg 15d located at its distal end 15b.

In its proximal region, the tubular wall 11 is further provided with an inner radial ridge 16 having an annular shape on the example shown. The inner radial ridge 16 has a sloped proximal face 16a, and a distal face 16b.

The housing 10 is open at its proximal end 10a which is provided with an outer flange 17. As will appear from the description below, this outer flange 17 may form a bearing surface for the fingers of the end-user at the time of delivery of the drug to be contained in the tubular barrel 30. The housing 10 is further provided at its proximal end 10a with a proximal inner rim 18, proximally spaced with respect to the inner radial ridge 16: the space located between the inner radial ridge 16 and the proximal inner rim 18 therefore forms an annular recess 19 within the inner wall of the housing 10.

Figures 4A, 4B:
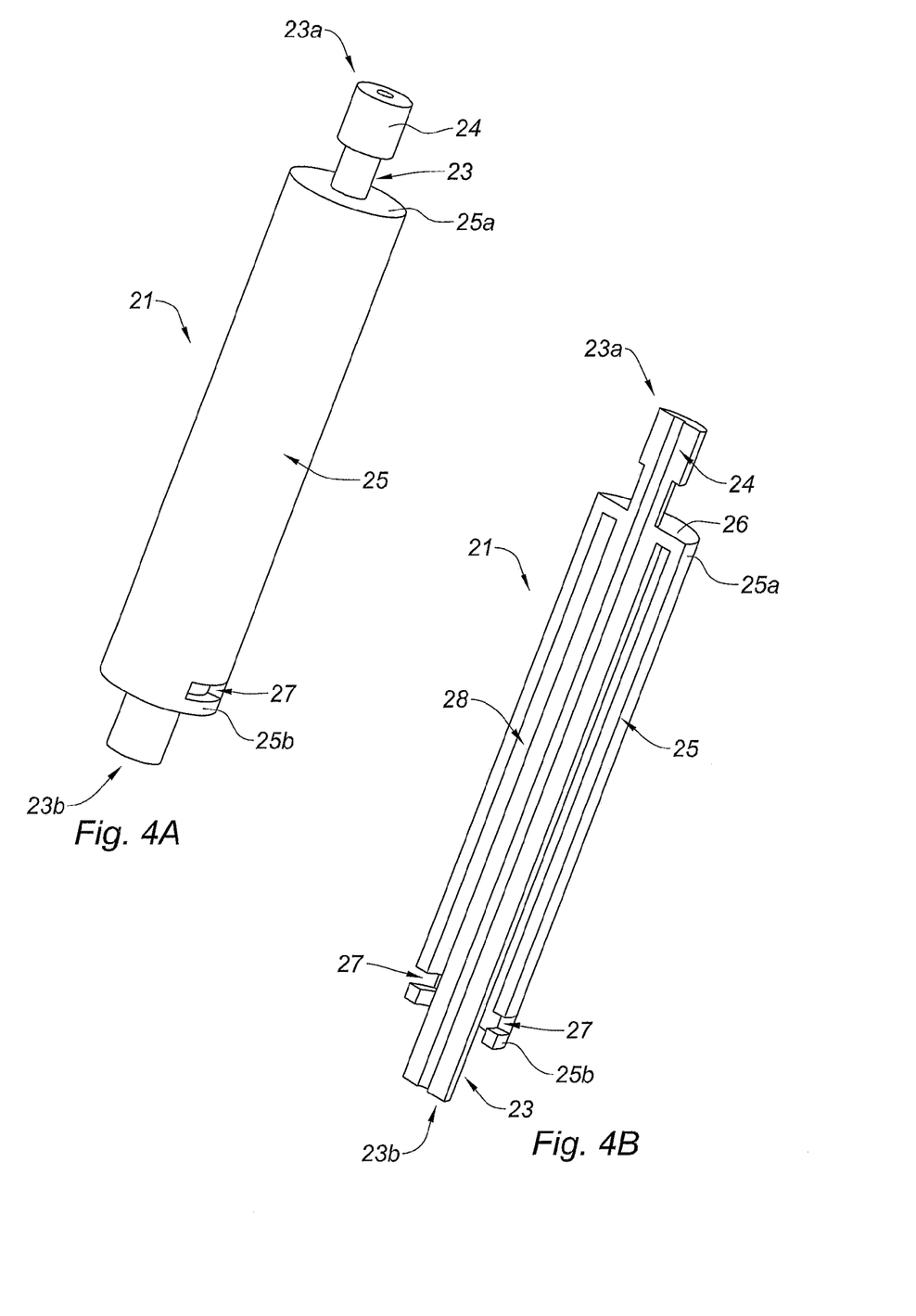
FIG. 4A is a perspective view of the needle hub of the device of FIG. 1.
FIG. 4B is a section view of the perspective view of FIG. 4A.

With reference to FIGS. 1, 4A and 4B, the needle hub 20 will now be described in detail. As appears from FIG. 1 the needle hub 20 comprises a first part, under the form, of an elongate element 21, and a second part, fixed at the proximal end of the elongate element 21 and which is a radially compressible part 22. The radially compressible part may be made of rubber or elastomeric material.

With reference to FIGS. 4A and 4B is shown the elongate element 21 of the needle hub 20. The elongate element 21 comprises a hollow shaft 23 for receiving the needle 2 therein. The hollow shaft 23 is provided at its proximal end 23a with an outer circular ridge 24. Distally spaced with respect to this outer circular ridge 24, is provided a tubular element 25 surrounding the hollow shaft 23 on a certain length, but not reaching the distal end 23b of the hollow shaft 23. The distal end 23b of the hollow shaft is dimensioned so as to be able to be received within the central hole 13 of the inner transversal wall 12 of the housing 10. The tubular element 25 is fixed to the hollow shaft 23 by means of a transversal wall 26 joining the proximal end 25a of the tubular element 25 to the hollow shaft 23. In its distal region, but proximally spaced with respect to its distal end 25b, the tubular element 25 is provided with two diametrically opposed circumferential windows 27.

With reference to FIG. 4B, the space located between the outer wall of the hollow shaft 23 and the inner wall of the tubular element 25 forms a tubular recess 28 closed at its proximal end and open at its distal end.

With reference to FIG. 1, the radially compressible part 22 of the needle hub 20 is mounted on the outer circular ridge 24 of the hollow shaft 23 of the elongate element 21. The needle 2 is received within the hollow shaft 23 and passes through the radially compressible part 22. The distal end 2b of the needle 2 extends beyond the distal end 20b of the needle hub 20 and the proximal end 2a of the needle 2 extends beyond the proximal end 20a of the needle hub 20.

As will appear from the following description, the tubular barrel 30 is dimensioned and shaped so that said tubular barrel 30, and in particular its distal end 30b, is capable of being received within the housing 10 and so that said tubular barrel 30, and in particular its distal end 30b, is also capable of receiving the needle hub 20. Indeed, in a first stage, once the tubular barrel 30 is pre-assembled on the housing 10, at least a part of the needle hub 20 substantially closes the distal end 30b of said tubular barrel 30, not in a tightly manner, this tubular barrel 30 being movable in translation and/or in rotation along said longitudinal axis with respect to the needle hub 20 and to the housing 10.

The use and operation of the drug delivery device 1 of the invention will now be explained with reference to FIGS. 5A to 9.

Figure 5A:
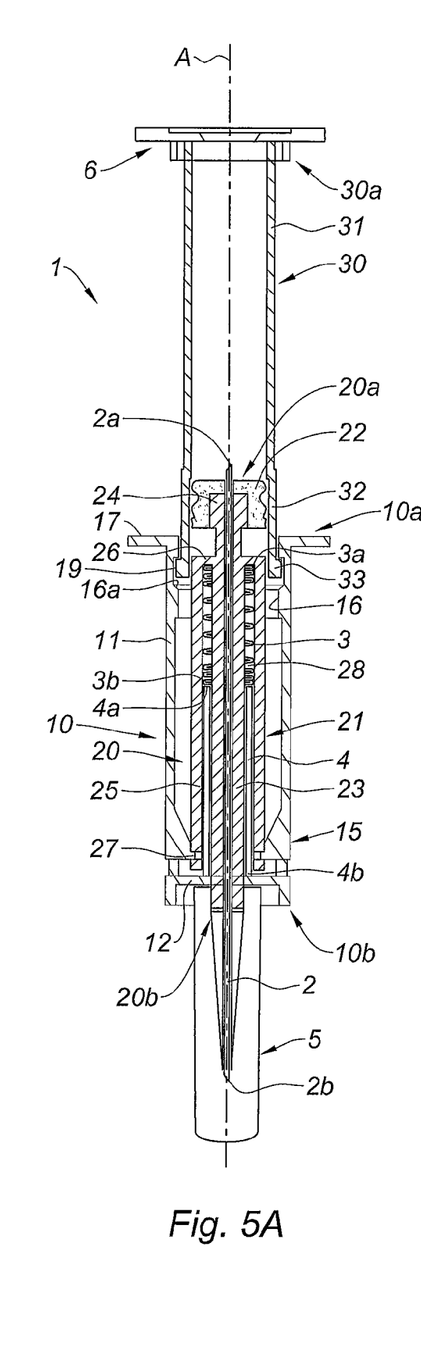
FIG. 5A is a cross section view of the device of FIG. 1 once the tubular barrel is pre-assembled on the housing.

On FIG. 5A, the prefillable drug delivery device 1 is in a storage configuration, in which it may be provided to pharmaceutical companies, with the tubular barrel 30 pre-assembled on the housing 10, with no tight contact between the tubular barrel 30 and the needle hub 20, and before any filling step. As appears from FIG. 5A, the tubular barrel 30 has been pre-assembled on the housing 30 by introducing the distal end 30b of the tubular barrel 30 within the proximal end 10a of the housing 10. The circular outer rim 33 of the tubular barrel 30 has been force fitted in order to overcome the proximal inner rim 18 of the housing 10, until said circular outer rim 33 reaches the annular recess 19 of the housing 10, as shown on FIG. 5A. The circular outer rim 33 and the annular recess 19 form therefore temporary holding means for maintaining the tubular barrel 30 pre-assembled on the housing. "Temporary holding means" means herein that the circular outer rim 33 and the annular recess 19 maintain the tubular barrel 30 in a pre-assembled position on the housing 10 as long as no sufficient force is exerted on said tubular barrel 30 in order to disengage the circular outer rim 33 from the annular recess 19 in the distal direction. Indeed, if a force capable of overcoming the resistance of the inner radial ridge 16 and/or the proximal inner rim 18 is applied on the tubular barrel 30 when it is in this pre-assembled position, the tubular barrel 30 can move in translation and/or in rotation with respect to the needle hub 20. Indeed, the proximal end 30a of the tubular barrel 30 may be provided with an outer flange 6 so as to facilitate the future distal pushing of the tubular barrel 30 by the user.

Figure 5B:
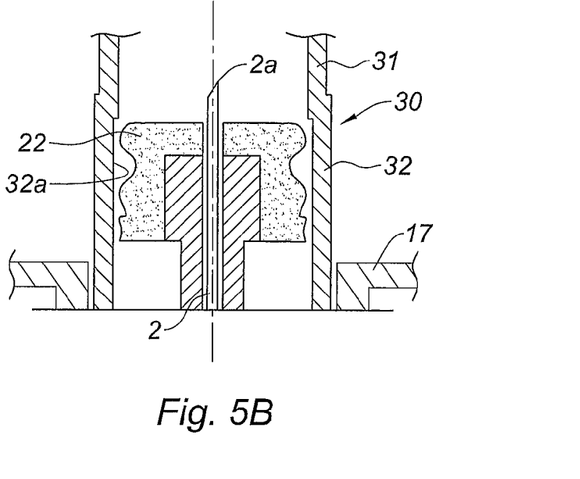
FIG. 5B is a partial enlarged view of FIG. 5A.

As appears also from FIG. 5B, which is an enlarged view of the part of FIG. 5A showing the position of the radially compressible part 22 of the needle hub 20 with respect to the tubular barrel 30, in the pre-assembled position of the tubular barrel 30, said radially compressible part 22 is lodged within the distal region 32 of the tubular barrel 30 and no sealing contact is realized between the inner wall 32a of this distal region 32 of the tubular barrel 30 and the radially compressible part 22 of the needle hub 20. As a consequence, as a space exists between the tubular barrel 30 and the needle hub 20, the needle hub 20 forms a distal closure of the tubular barrel 30, but there is no tight contact between the respective surfaces of these two elements.

Still with reference to FIG. 5A where the device 1 of the invention is in a storage position, the housing 10 receives the needle hub 20, so that the inner radial pegs 15d of the flexible legs 15 of the housing 10 are engaged within the circumferential windows 27 of the needle hub 20. In addition, the needle hub 20 receives the helical spring 3 and the sleeve 4 within its tubular recess 28, the helical spring 3 being located proximally with respect to the sleeve 4. The sleeve 4 has the shape of a regular tube and its distal end 4b bears on the proximal face of the inner transversal wall 12 of the housing 10. In the storage position of the device 1 as shown on FIG. 5A, the helical spring 3 is in a stressed state and its proximal end 3a bears on the distal face of the transversal wall 26 of the needle hub 20 while its distal end 3b bears on the proximal end 4a of the sleeve 4. In this position, the inner radial pegs 15d of the flexible legs 15 of the housing 10 and the circumferential windows 27 of the needle hub 20, by being engaged in one another, form retaining means for maintaining the helical spring 3 in its stressed state, and therefore for maintaining the housing 10 in its retracted position.

In the storage position of the device 1 as shown on FIG. 5A, the housing 10 is in its retracted position with respect to the needle hub 20, and the distal end 2b of the needle 2 extends beyond the distal end 10b of the housing 10. In this storage position, the distal end 2b of the needle 2 is covered with a protection cap 5 in order to avoid potential accidental needlestick injuries.

As mentioned above, the drug delivery device 1 as shown on FIG. 5A does not contain any drug and needs to be filled with the drug to be delivered. The drug delivery device 1 may be provided to the pharmaceutical companies in its storage position as shown on FIG. 5A, with the tubular barrel 30 pre-assembled on the housing 10, and no sealing contact existing between the tubular barrel 30 and the needle hub 20. As a result, the pre-assembly of the tubular barrel 30 and the needle hub 20 can be realized under non-sterile manufacturing conditions, the whole drug delivery device being sterilized latter on, before the filling step with the pharmaceutical drug.

Before proceeding to the filling step, the sealing contact between the tubular barrel 30 and the needle hub 20 must be realized, so that the needle hub 20, and in particular its radially compressible part 22, performs a safe and sealed distal closure of the tubular barrel 30. In this view, the tubular barrel 30 is further pushed distally, for example via a user exerting a distal force on the outer flange 6 of the tubular barrel 30, on a limited distance so that the circular outer rim 33 overcomes the sloped proximal face 16a of the inner radial ridge 16 and eventually overcomes the inner radial ridge 16 itself.

Figure 6:
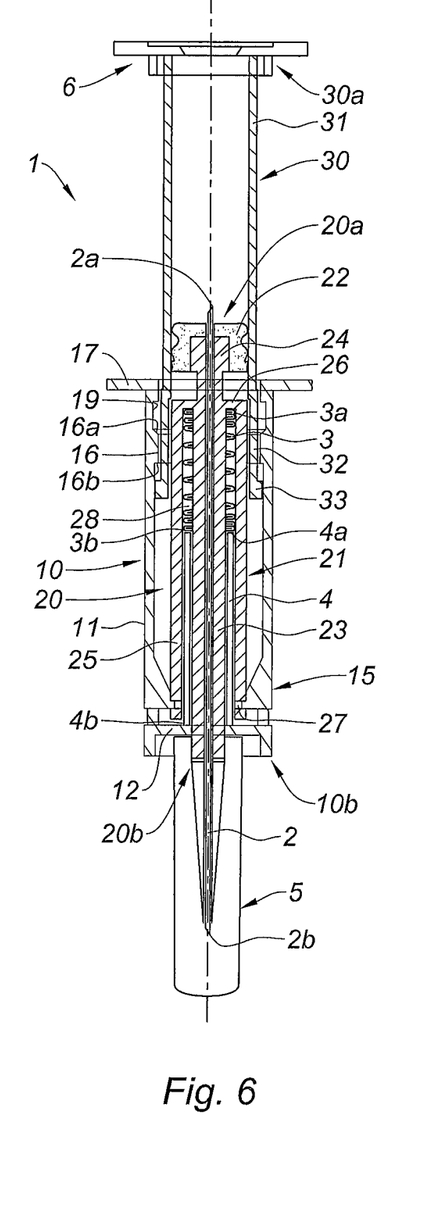
FIG. 6 is a cross section view of the device of FIG. 1 once the sealing means are in their active state, the tubular barrel being in a before use position.

As shown on FIG. 6, the limited distal movement of the tubular barrel 30 with respect to the needle hub 20 has caused the radially compressible part 22 of the needle hub 20 to enter the restricted portion 31 of the tubular barrel 30. In this position, the radially compressible part 22 is radially compressed by the inner wall of the restricted portion 31 of the tubular barrel 30 and therefore a tight contact is created between the needle hub 20 and the tubular barrel 30. The restricted portion 31 of the tubular barrel 30 and the radially compressible part 22 of the needle hub 20 therefore form sealing means for realizing sealing contact between the tubular barrel 30 and the needle hub 20, these sealing means being caused to go from an inactive state, as shown on FIG. 5A and in which said sealing contact is not present, to an active state, as shown on FIG. 6 and where sealing contact is performed, under the effect of a limited movement, a distal limited movement on the example shown, of the tubular barrel 30 with respect to the needle hub 20.

With reference to FIG. 6, it appears that, should the tubular barrel 30 be pulled in the proximal direction, then the circular outer rim 33 would come in abutment against the distal face 16b of the inner radial ridge 16. The circular outer rim 33 and the inner radial ridge 16 therefore form securing means for preventing the sealing means from returning to their inactive state, once they are in their active state. This position of the tubular barrel 30, where the circular outer rim 33 is in abutment against the distal face 16b of the inner radial ridge is therefore the most proximal position possible for the tubular barrel 30 once the sealing means have reached their active state, and will be referred to in the present application as the proximal position of the tubular barrel.

In the active state of the sealing means, the needle hub 20, and in particular its radially compressible part 22, realizes sealing contact with the tubular barrel 30. The needle hub 20, and in particular its radially compressible part 22, is still capable of sliding along the inner wall of the tubular barrel 30 and of moving in translation with respect to the tubular barrel 30. The radially compressible part 22 may be made of rubber or elastomeric material and acts as a stopper. As such, the tubular barrel 30 is movable in translation with respect to the needle hub 20 from its proximal position in the distal direction.

When the tubular barrel 30 is assembled on the housing 10 and the sealing means are in their active state, sealing contact is realized between the distal end of the tubular barrel 30 and the radially compressible part of the needle hub 20, and the tubular barrel 30 may then be filled with a drug. The filling step is preferably completed in the premises of the pharmaceutical company producing the adequate drug, preferably on assembly lines.

The position of the tubular barrel 30 with respect to the needle hub 20 during the filling step, herein called the filling position of the tubular barrel, may correspond to the proximal position of the tubular barrel 30 as defined above, or alternatively to a position slightly distally spaced from said proximal position in particular in order to allow the completion a vein test before the delivery step. For example, on FIG. 7, the filling position of the tubular barrel 30 is slightly distally spaced from the proximal position of the tubular barrel: in this filling position of the tubular barrel 30, the circular outer rim 33 is preferably slightly distally spaced with respect to the inner radial ridge 16, so as to create a free space 9 located between said inner radial ridge 16 and the circular outer rim 33. Once the tubular barrel 30 has been filled with the drug 7 and once the needle 2 has been inserted in the injection site (not shown), this free space 9 allows the tubular barrel 30 to be slightly pulled in the proximal direction, in order to check whether the needle 2 has reached a vein or not (the vein test).

Once the tubular barrel 30 is filled with the adequate volume of drug 7, a stopper 8 is used for closing the proximal end 30a of the tubular barrel 30.

Figure 7:
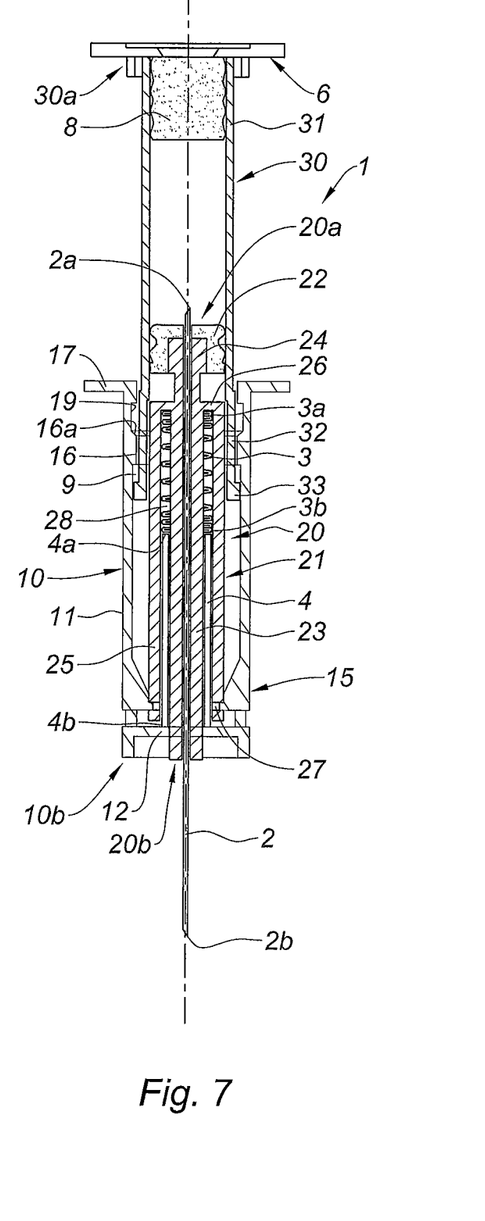
FIG. 7 is a cross section view of the device of FIG. 6 once it has been prefilled with a drug to be delivered.

The drug delivery device 1 may then be provided to the end-user as a prefilled drug delivery device, as shown on FIG. 7, with preferably a cap, like cap 5 of FIG. 6, for protecting the needle (not shown on FIG. 7) and hermetically closing the device 1.

When the end-user is ready for starting the delivery of the drug, he removes the cap 5 (FIG. 6) so as to uncover the needle 2, as shown on FIG. 7. In the position shown on FIG. 7, before the delivery has started, the tubular barrel 30 is still in its filling position. Once the needle 2 has been correctly inserted in the injection site, the delivery of the drug 7 as such may start by pushing distally on the tubular barrel 30 via the outer flange 6. Since the proximal end 2a of the needle 2 protrudes in the tubular barrel 30, the drug 7 is caused to be expelled from the tubular barrel 30 by entering the proximal end 2a of the needle 2 and exiting via its distal end 2b.

Figure 8:
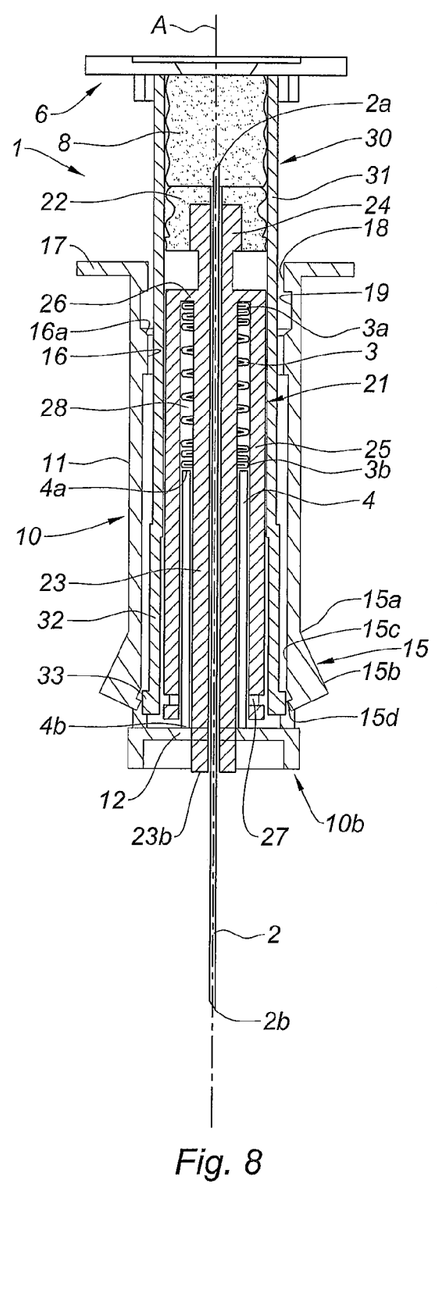
FIG. 8 is a cross section view of the device of FIG. 7 at the end of the delivery of the drug.

As shown on FIG. 8, when the tubular barrel 30 reaches a distal position corresponding to a position when substantially all the drug 7 contained in the tubular barrel 30 has been expelled, and herein called the end-of-delivery position of the tubular barrel, the circular outer rim 33 located at the distal end 30b of the tubular barrel 30 comes in contact with the sloped proximal face 15c of the flexible legs 15 which are consequently caused to outwardly radially deflect. The radial pegs 15d therefore disengage from the circumferential windows 27 of the hollow shaft 23 of the needle hub 20. As a consequence, when the end-user removes the drug delivery device 1 from the injection site, the helical spring 3 is no more maintained in it stressed state and it tends to come back to an expanded state corresponding to its natural rest state. The sloped proximal face 15c of the flexible legs 15, the distal end 30b and the circular outer rim 33 of the tubular barrel 30 therefore form deactivating means of the retaining means when the tubular barrel 30 reaches its end-of-delivery position.

While expanding, the helical spring 3 pushes the sleeve 4 in the distal direction; the sleeve 4 therefore pushes the housing 10 in the distal direction via its distal end 4b being in contact with the transversal wall 12 of the housing 10. The housing 10 is therefore moved automatically by the helical spring 3 to its protection position, in which the distal end 2b of the needle 2 no more extends beyond the distal end 10b of the housing 10, as shown on FIG. 9. As a result no further action from the user is required to active the safety system for protecting the needle after injection.

Figure 9:
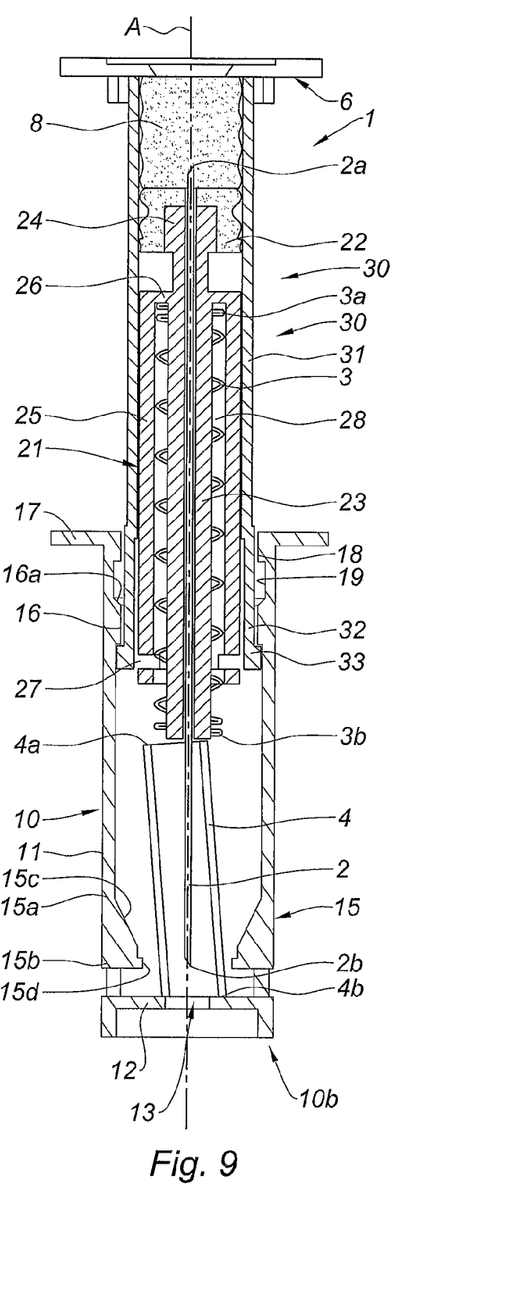
FIG. 9 is a cross section view of the device of FIG. 8 once the needle protection sleeve is in its protection position.

In addition, during the expansion of the helical spring 3, the sleeve 4 has escaped the tubular recess 28 of the needle hub 20 and is no more maintained aligned on the longitudinal axis of the device 1, as shown on FIG. 9. In this slanted position, the sleeve 4 forms a locking means of the housing 10 in its protection position, as the sleeve 4 now prevents the housing 10 from being moved back to its retraction position.

The drug delivery device 1 of the invention is therefore particularly safe, even once the delivery of the drug has been completed. Its global size is particularly compact and allows low-cost storage, efficient transportation and is easy to integrate with current pharmaceutical filling systems. In addition, the prefillable drug delivery device of the invention includes an integrated needle safety system, under the form of the housing: the pharmaceutical companies do not have to handle any assembling step of the needle safety system and may focus on the filling step only. The prefillable drug delivery device constitutes therefore an improvement for these pharmaceutical companies which may be able then to increase their productivity.

The invention claimed is:

1. Prefillable drug delivery device, comprising:
a housing at least partially receiving a needle hub, said housing being movable with respect to said needle hub between a retracted position, in which a distal end of said needle hub extends beyond a distal end of said housing, and a protection position, in which the distal end of said needle hub does not extend beyond the distal end of said housing,
a tubular barrel for receiving a drug, said tubular barrel having an open proximal end and an open distal end, said tubular barrel being capable of being pre-assembled on said housing via its distal end so that at least part of said needle hub substantially closes the distal end of said tubular barrel, said tubular barrel being movable in translation and/or in rotation along a longitudinal axis with respect to said needle hub and to said housing,
wherein said device further comprises a sealing member actionable once said tubular barrel is pre-assembled on said housing, said sealing member capable of transitioning from an inactive state in which no sealing contact is present between said part of said needle hub and an inner wall of said tubular barrel, to an active state, in which sealing contact is made between said part of said needle hub and the inner wall of said tubular barrel,
wherein, in the active state of said sealing member, said tubular barrel is movable in translation with respect to said needle hub between a filling position, in which the tubular barrel may be filled with the drug to be delivered, and an end-of-delivery position, distally spaced with respect to said filling position, in which said drug potentially received within said tubular barrel has been substantially expelled from said tubular barrel via a needle.

2. The prefillable drug delivery device according to claim 1, wherein said needle hub bears the needle, and said needle hub and needle being substantially aligned on said longitudinal axis, wherein a distal end of said needle extends beyond the distal end of said housing when said housing is in its retracted position, and the distal end of said needle does not extend beyond the distal end of said housing when said housing is in the protection position.

3. The prefillable drug delivery device of claim 2, wherein a proximal end of a needle extends proximally beyond a proximal end of said needle hub.

4. The prefillable drug delivery device according to claim 1, further comprising a temporary holding member for maintaining said tubular barrel pre-assembled on said housing before activation of the sealing member.

5. The prefillable drug delivery device according to claim 4, wherein said temporary holding member comprises an outer rim located on an outer wall of the distal part of the tubular barrel and an annular recess located on an inner wall of said housing, said outer rim being engaged in said annular recess when said tubular barrel is pre-assembled on said housing, said outer rim being disengageable from said annular recess under the effect of movement of said tubular barrel with respect to said needle hub.

6. The prefillable drug delivery device according to claim 1, wherein said sealing member transitions from the inactive state to the active state by movement of said tubular barrel with respect to said needle hub.

7. The prefillable drug delivery device according to claim 1, wherein a portion of the sealing member is located on the tubular barrel and a portion of the sealing member is located on the needle hub.

8. The prefillable drug delivery device according to claim 1, further comprising a securing member for preventing said sealing member from returning to the inactive state once transitioned to the active state.

9. The prefillable drug delivery device according to claim 8, wherein a portion of said securing member is located on the tubular barrel and a portion of said securing member is located on the housing.

10. The prefillable drug delivery device according to claim 8, wherein the securing member comprises an outer rim and a radial ridge distally spaced with respect to an annular recess on an inner wall of said housing, said radial ridge being provided with a sloped proximal face, said outer rim being capable of overcoming said sloped proximal face under the effect of a distal movement of said tubular barrel with respect to the needle hub, thereafter said outer rim being in proximal abutment against said radial ridge once a sealing means is in the active state and a proximal force is exerted on said tubular barrel.

11. The prefillable drug delivery device according to claim 1, wherein the sealing member comprises a radially compressible part of said needle hub, and a restricted portion of an inner wall of said tubular barrel, said sealing member transitioning to the active state when said restricted portion faces said radially compressible part under the effect of distal movement of said tubular barrel with respect to the needle hub, said restricted portion thereby compressing said radially compressible part and generating sealing contact between said needle hub and the inner wall of said tubular barrel.

12. The prefillable drug delivery device of claim 1, further comprising a retainer for maintaining said housing in the retracted position until the tubular barrel reaches the end-of-delivery position.

13. The prefillable drug delivery device according to claim 12, further comprising a deactivating member for releasing said retainer when said tubular barrel reaches the end-of-delivery position.

14. The prefillable drug delivery device according to claim 13, further comprising a biasing member for automatically moving the housing from the retracted position to the protection position, said biasing member being maintained in a stressed state by said retainer, in which the housing is in the retracted position and transitionable to an expanded state, in which said housing is in the protection position, when said retainer is released.

15. The prefillable drug delivery device according to claim 14, wherein the retainer comprises flexible legs located on said housing and capable of being radially deflected from a rest position, in which the flexible legs maintain said biasing member in the stressed state, to a deflected position, in which the biasing member is free to expand, and wherein the deactivating member comprises the distal end of said tubular barrel, said distal end coming in contact with and radially deflecting said flexible legs when said tubular barrel reaches the end-of-delivery position, thereby freeing the biasing member which moves the housing to the protection position.

16. The prefillable drug delivery device of claim 1, further comprising a lock for preventing said housing from being moved back to the retracted position once the housing has been transitioned to the protection position.

17. The prefillable drug delivery device of claim 1, wherein the proximal end of said tubular barrel further comprises an outer flange forming a pushing surface for a user to exert a distal pressure on said tubular barrel.

18. The prefillable drug delivery device of claim 1, in which said tubular barrel is assembled on said housing and said sealing member is in the active state, wherein at least a portion of the tubular barrel located proximally to the needle hub is filled with a drug to be delivered, and wherein the proximal end of said tubular barrel is closed with a stopper.

19. The prefillable drug delivery device of claim 1, wherein the tubular barrel is configured to be filled via the open proximal end of the tubular barrel.

20. The prefillable drug delivery device of claim 19, further comprising a stopper configured for closing the proximal end of the tubular barrel once the tubular barrel has been filled.

\* \* \* \* \*